US00PP24288P3

(12) United States Plant Patent
Korlipara

(10) Patent No.: US PP24,288 P3
(45) Date of Patent: Mar. 4, 2014

(54) *COREOPSIS* PLANT NAMED 'PINK SAPPHIRE'

(50) Latin Name: ***Coreopsis* sp.**
Varietal Denomination: Pink Sapphire

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 115 days.

(21) Appl. No.: 13/506,803

(22) Filed: May 16, 2012

(65) Prior Publication Data

US 2013/0312144 P1 Nov. 21, 2013

(51) Int. Cl.
*A01H 5/00* (2006.01)

(52) U.S. Cl.
USPC ..... Plt./417

(58) Field of Classification Search
USPC ..... Plt./417
See application file for complete search history.

(56) References Cited

PUBLICATIONS

UPOV PLUTO QZ Citation for 'Pink Sapphire' Feb. 15, 2013.*

* cited by examiner

*Primary Examiner* — Wendy C Haas
(74) *Attorney, Agent, or Firm* — Klarquist Sparkman, LLP

(57) ABSTRACT

A new and distinct *Coreopsis* plant named 'Pink Sapphire' characterized by daisy-type flowers that grow to 4.5 cm in diameter, purple pink flowers with a light eye, grass green foliage on strong, upright, short stems, flowering for the whole summer, and a dense, upright habit.

1 Drawing Sheet

Botanical denomination: *Coreopsis* sp.
Variety designation: 'Pink Sapphire'.

BACKGROUND OF THE INVENTION

The present invention relates to a new and distinct cultivar of *Coreopsis* and given the cultivar name 'Pink Sapphire'. *Coreopsis* is in the family Asteraceae. This new cultivar originated from an open pollinated cross of *Coreopsis* 'Garnet' (U.S. Plant Pat. No. 22,485), as the seed parent. Compared to the seed parent, *Coreopsis* 'Garnet', the new cultivar is slightly larger in habit with flowers that are bright pink rather than deep rose. The flowers of the new cultivar are larger and have a light eye rather than a dark eye.

Compared to *Coreopsis rosea*, an unpatented plant, the flowers on the new cultivar are purple pink with a light eye rather than pink. In addition the new cultivar has larger flowers, blooms earlier, and is upright rather than floppy.

SUMMARY OF THE INVENTION

The following traits have been repeatedly observed and are determined to be the unique characteristics of the new variety. These characteristics in combination distinguish *Coreopsis* 'Pink Sapphire' as a new and distinct cultivar:

1. large daisy-type flowers that grow to 4.5 cm in diameter,
2. purple pink flowers with a light eye,
3. grass green foliage on strong, upright, short stems,
4. flowering for the whole summer, and
5. a dense, upright habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows nine-month-old *Coreopsis* 'Pink Sapphire' growing in the ground in the trial field in August in Canby, Oreg.

DETAILED PLANT DESCRIPTION

The following is a detailed description of the new *Coreopsis* cultivar based on observations of nine-month-old specimens growing in the ground in full sun under typical outdoor conditions in the trial fields in July in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 6 to 9.
*Size.*—40 cm wide and 40 cm tall to top of inflorescences.
*Form.*—Upright mound.
*Vigor.*—Excellent, fills a one gallon container in six to eight weeks.
*Roots.*—Fibrous, stems root easily from stem cuttings.

Stem:

*Type.*—Ascending.

*Size.*—20 cm tall to where branches for flowering and 4 mm wide.

*Number of stems from the crown.*—About 9.

*Internode length.*—2 cm to 6 cm.

*Surface.*—Glabrous.

*Color.*—Yellow Green 146A except at base where tinted Greyed Purple 187B.

Leaf:

*Type.*—Simple.

*Size.*—Grows to 10.5 cm long and 3 cm wide.

*Lobing.*—0 to 3 pinnatifid, lobes linear, the terminal lobe the longest, terminal lobes each lobe 2 mm to 7 mm wide and 25 mm to 80 mm long, side lobes 1 mm to 3 mm wide and 15 mm to 36 mm long.

*Arrangement.*—Opposite.

*Margins.*—Entire.

*Apex.*—Acute.

*Venation.*—Pinnate.

*Surface texture.*—Pubescent on both sides.

*Petiole.*—Length 5 mm to 20 mm, width 1 mm to 2 mm, margins pubescent, glabrous Yellow Green 146A.

*Color.*—Top and bottom side Yellow Green 146A.

Inflorescence:

*Type.*—Long stalked terminal heads of daisy type inflorescences.

*Peduncle.*—10 cm long, 1 mm wide, glabrous, Yellow Green 146A.

*Size.*—Grows to 4.5 cm wide and 10 mm deep.

*Immature.*—5 mm deep and 6 mm wide, ovoid, glabrous, top streaked Greyed Purple 187A, Greyed Orange 167A, and Yellow Green 146A; bottom Yellow Green 146A.

*Receptacle.*—Disc shaped, 3 mm wide and 2 mm deep, Yellow Green 146B.

*Phyllary.*—In two series; inner series broadly campanulate with 8 lobes, grows to 17 mm wide and 3 mm deep, each lobe ovate, margin entire, tip acute, glabrous on both sides, 4 mm long and 4 mm wide; topside Greyed Orange 167B edged with Greyed Purple 187A, bottom side top half Greyed Orange 167B, bottom half Yellow Green 146B; outer series stellate, with 8 lobes, grows to 2 mm wide and 2 mm deep, each lobe ovate, margin entire, tip acute, glabrous on both sides, Green 137A on both sides with tips Greyed Purple 187A.

*Lastingness.*—Each inflorescence lasts about a week on the plant.

Florets:

*Type.*—Composite.

*Ray florets.*—8 in number with no pistil or stamen, obovate with the tip three lobed with lobes obtuse and notched and the central lobe the longest and most notched, entire on both sides, grows to 23 mm long, 9 mm wide, glabrous, topside Red Purple N74A with basal eye White 155A; bottom side Red Purple N74C with basal eye White 155A.

*Disc.*—Conic, deeper with maturity, 5 mm wide and becoming 4 mm deep with maturity; Greyed Purple 185A.

*Disc florets.*—With stamen and pistil, about 110 in number, 4 mm long and 1.5 mm wide, tubular; corolla 3 mm long, inside and out tube Yellow Orange 16B, 4 lobes Greyed Purple 185A; pistil 1, ovary 1 mm long, White 155D, style 4 mm long, extruding, with 2-branched stigma, stigma and style Greyed Purple 187B; stamen 5, anthers 2 mm long, Greyed Purple N187A, no pollen.

*Bloom period.*—June through October in Canby, Oreg.

*Fragrance.*—None.

*Seed.*—None seen.

*Fertility.*—Infertile.

Disease and pests: Plants of the new *Coreopsis* have not been shown to be resistant to pathogens and pests common to *Coreopsis*.

I claim:

1. A new and distinct *Coreopsis* plant as herein illustrated and described.

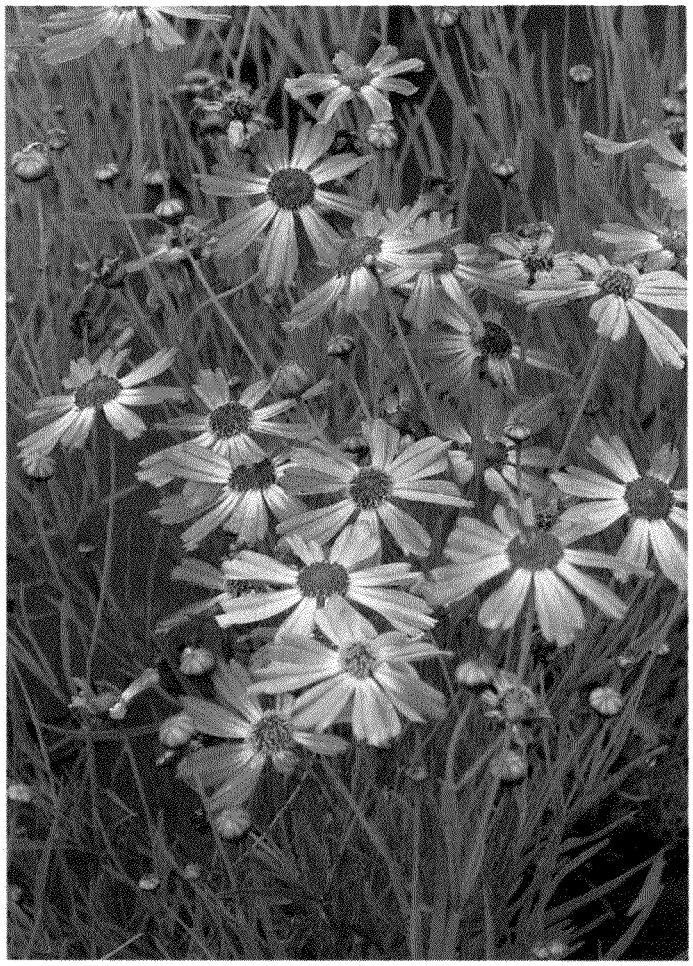

* * * * *